US00PP07880P

United States Patent [19]

Cripps

[11] Patent Number: Plant 7,880

[45] Date of Patent: Jun. 9, 1992

[54] APPLE TREE CRIPPS PINK CULTIVAR

[75] Inventor: John E. Cripps, Florent Park, Australia

[73] Assignee: Western Australia Department of Agriculture, South Perth, Australia

[21] Appl. No.: 599,347

[22] Filed: Oct. 18, 1990

[51] Int. Cl.[5] ..... A01H 5/00
[52] U.S. Cl. ..... Plt./34
[58] Field of Search ..... Plt. 34

*Primary Examiner*—James R. Feyrer
*Attorney, Agent, or Firm*—Chernoff, Vilhauer, McClung & Stenzel

[57] ABSTRACT

A new variety of apple tree selected from a seedling population of a planned cross, characterized by the taste, flavor and aroma of its high dessert quality sunburn-resistant fruits which have good cold storage and retail shelf life.

5 Drawing Sheets

BACKGROUND AND SUMMARY OF THE INVENTION

This invention relates to a new and distinct variety of apple tree which was selected from a population of seedlings resulting from a planned cross between the varieties Lady Williams (unpatented chance seedling discovered in Western Australia) and Golden Delicious (unpatented chance seedling discovered in the State of West Virginia). The crosses were made in 1973 by John Cripps, Senior Research Officer, Western Australia Department of Agriculture at the Manjiump Horticultural Research Centre in Western Australia.

The new seedling variety first fruited in 1979 and was subsequently selected for propagation and further testing. Second and third generation trees have now borne fruit. It since has been recognized and selected as a new and improved apple variety which is distinctive from its parents as well as from all other apple varieties. The variety produces large asymmetrical, uniquely flavored apples with a partial pink-red blush on a yellow-green background which mature in early May in Western Australia. Its distinctive features include:

1. A strong upright growth form and habit similar to that exhibited by its parent Lady Williams.
2. Low winter chilling requirements.
3. The ability to flower and fruit precociously and set fruit on one-year old upright growth.
4. Fruit having high tolerance to sunburn and a medium to thin skin which doesn't crack.
5. Fruit having a smooth fine flesh texture which resists browning after being cut and exposed to air.
6. Fruit having high soluble sugars.
7. Fruit having an ability to retain long retail shelf life.
8. Fruit having a long cold storage life of up to six months allowing marketing flexibility.

Preliminary cold storage tests on apples harvested from three-year old trees grown at the Manjiump Research Centre indicate that this variety does not develop a bitter pit and is highly tolerant to cold storage.

The variety has inherited the sunburn resistance, low chilling requirements and the strong upright growth habit exhibited by one of its parents (Lady Williams) and the excellent fruit quality (high sugar, crisp juicy flesh, thin skin and aromatic flavor) of both of its parent varieties.

The new seedling variety has been reproduced asexually by budding and grafting. All subsequent asexually produced generations have been true to form in both their growth and fruiting characteristics and show that the foregoing characteristics come true and are established and transmitted through succeeding propagations and generations.

The following Drawings and Detailed Description of the Invention are taken from twenty (20) progeny trees in their third leaf year at the Manjiump Horticultural Research Centre during the summer of 1988.

Figure 1:
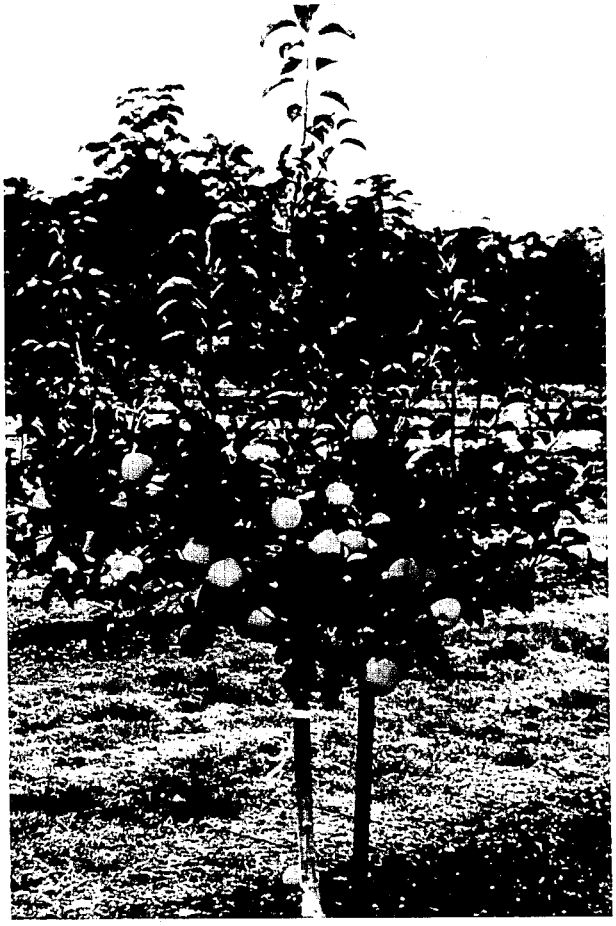
FIG. 1 shows the new variety apple tree bearing fruit.
Figure 2:
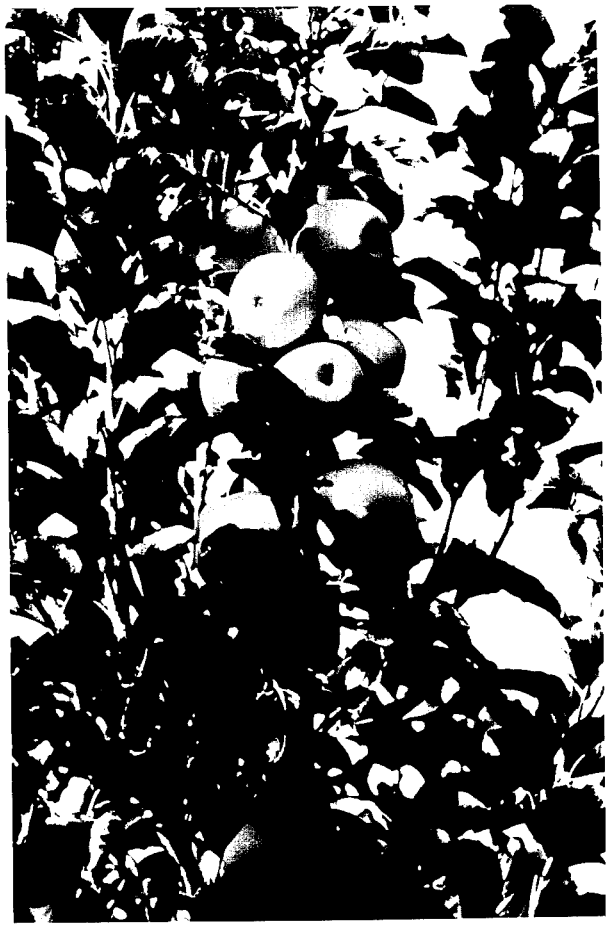
FIG. 2 is a close-up of one branch of the new variety bearing fruit.
Figure 3:
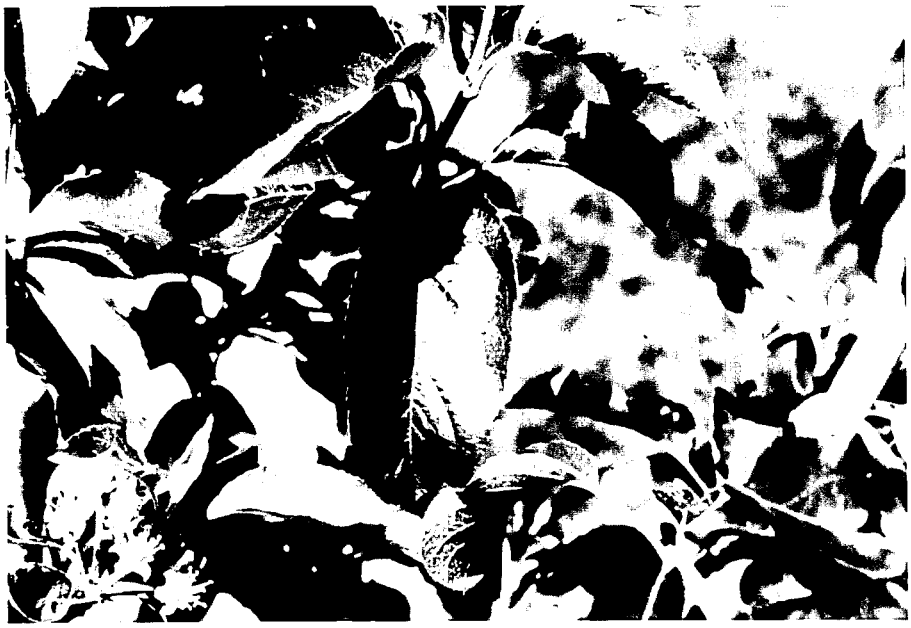
FIG. 3 shows the foliage of the new variety.
Figure 4:
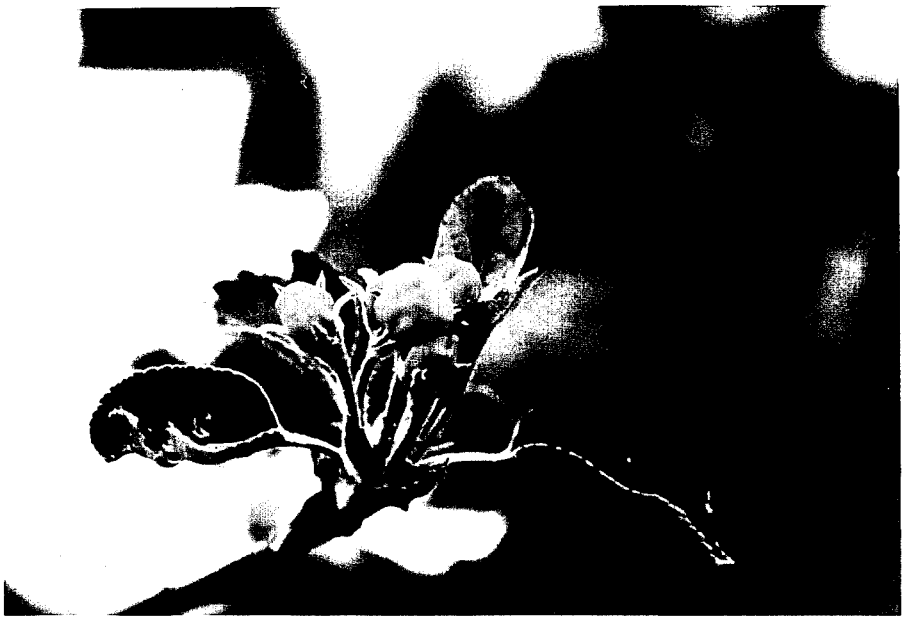
FIG. 4 shows the flowers of the new variety in bud stage.
Figure 5:
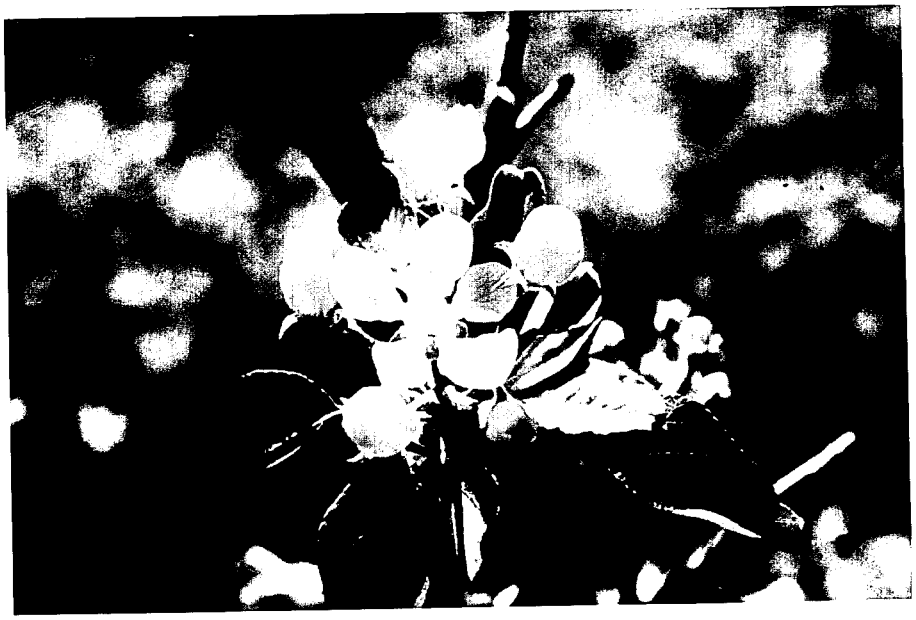
FIG. 5 shows the flowers of the new variety as the buds break.
Figure 6:
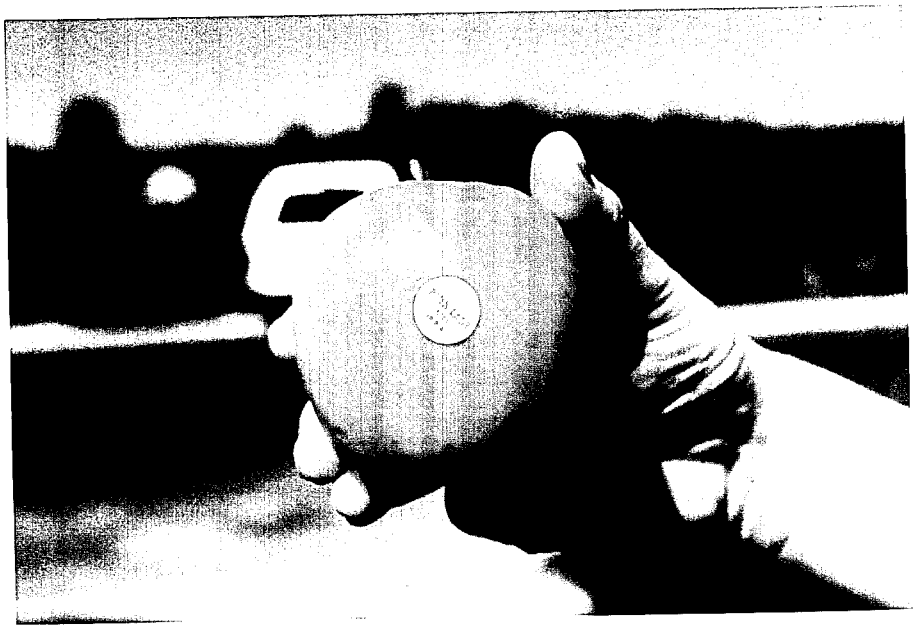
FIG. 6 is a close-up of the side of fruit grown on the new variety.
Figure 7:
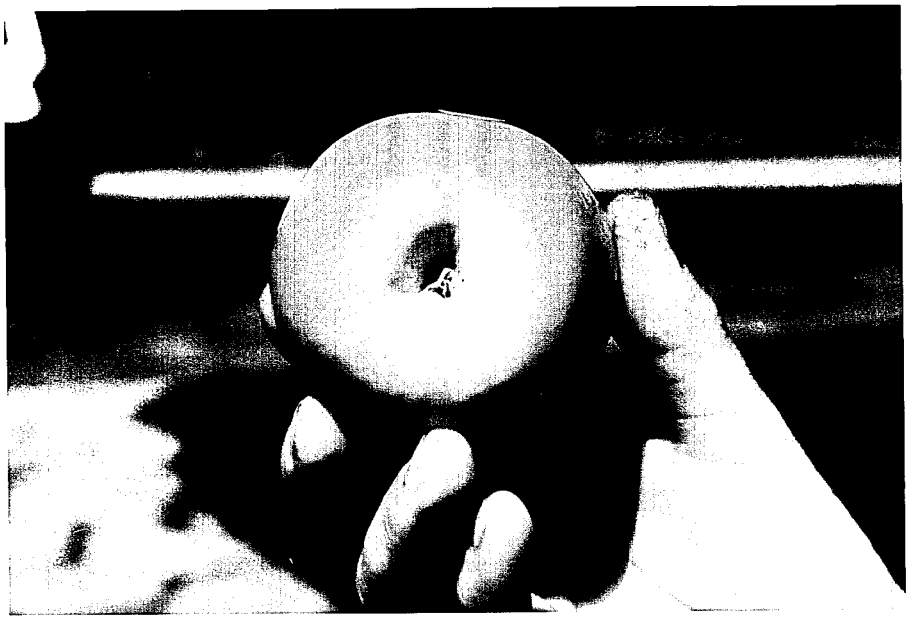
FIG. 7 is a close-up of the top of fruit shown on the new variety.

The following is a detailed description of the new apple variety with color terminology in accordance with the *Munsell Color Cascade Chart* except where general color terms of ordinary dictionary significance are used.

DETAILED DESCRIPTION OF THE INVENTION

Parentage: A cross of "Golden Delicious" and "Lady Williams" apple varieties.

Locality where grown and observed: Manjiump Horticultural Research Centre, Western Australia.

Dates of first and last pickings: About May 1 and May 10, respectively.

Tree: Medium to large with dense foliage. Upright habit, unpruned height to width ratio approximately 1.5 to 1.0 after 3 years.

*Vigor.*—Very vigorous, young trees average about 1.9 meters of new growth during the growing season in the nursery row following bud placement.

*Trunk.*—Medium stocky, smooth.

*Branches.*—Thick, smooth, upright.

*Branching habit.*—Much branched with average branching angles (inside measurement) of 45°-50° if allowed to grow naturally.

*Pruning and training requirements.*—Dependent upon the dwarfing ability fo the rootstock used. Adaptable to several styles, but best suited to "central leader" or "slender spindle" type training.

*Thinning requirements.*—Not subject to the annual bearing habits of some apple cultivars. Use of common chemical thinning methods for non-annual bearing varieties should be employed.

*Color.*—Green-brown (22-14).

*Shape of tipbud.*—Rounded.

*Lenticels.*—Numerous, medium large.

Leaves: Large, wide, long, oval, convex, pointed, medium thick, smooth.

*Length.*—108 mm (from 4th to 6th fully expanded).

*Width.*—67 mm (from 4th to 6th fully expanded).

*Color.*—Green (20-12), medium glossy on upper surface, green (20-10) with weak pubescence on lower surface.

*Margin.*—Finely serrate, crenate.

*Petiole.*—Long, medium slender, pubescent. Color — Light green (21-10).

*Stipule.*—Small.

*Central leaf vein.*—Color — light green (19-6) with pink tinge towrad basal end.

Flowers: Late, large.

*Dates of first and full bloom.*—About October 10 and November 10, respectively. The subject variety has a prolonged flowering season. Consequently there is no distinct flowering phase which can be classified as early, mid or late. It continues to flower moderately with a progression of flowering buds which open through a four to six week (October/November) flowering season. Since this cultivar has not been grown in the USA, no blooming or harvest dates are available for local conditions.

*Size.*—Medium to large.

*Color.*—Red (closed) then pink (open).

*Dormant fruit bud shape.*—Conical.

Position of margin of petals.—Free to touching.

Fruit:

*Maturity when described.*—Eating ripe.

*Size.*—Large, uniform. Length — about 78.3 mm Breadth — about 82.1 mm Mean fruit weight — about 195 grams.

*Production.*—Fifth year trees at Manjiump Horticultural Centre bore 4 bushels per tree per year with average crop size of 88-100 count.

*Coloration.*—Fruit has a striking pink blush (absent of striping) covering 30-80% of the apple surface. The pink blush coloration develops gradually in the late season and overlies a yellow-green background. Coloration continues to increase before the harvest season and even as fruits are harvested if the fruits are exposed to sunlight. Coloration is fuller for apples exposed to full sunlight than fruit hanging in shaded areas.

*Form.*—Asymmetrical, ellipsoid prominent ribbed surface. Medium distal crowns, rounded at base, sides slightly unbroken, unequal.

*Axis.*—Nonvertical.

*Cavity.*—Acute, deep, medium width, symmetrical, greenish, with very slight unbroken russet.

*Basin.*—Medium crown, ribbed, wide, open, medium depth. Markings — None.

*Sepals.*—Medium, touching.

*Stem.*—Medium length, medium thickness, not lipped. Length — 20-25 mm. Breadth — 5-6 mm.

*Calyx.*—Closed, V-shaped, medium width and medium depth. Calyx lobes — Reflexed and divergent. Pubescence — None.

*Skin.*—Bumpy, greasy. Bloom — absent. Craking tendency — absent. Thickness — medium. Ground color — yellow-green (23-8). Percentage of red overcolor — 50% to 60%. Overcolor of skin — red (39-12). Russet — none. Lenticels — medium, numerous, roundish.

*Flesh.*—Juicy, firm. Color — Creme. Texture — Firm. Flavor — Sub acid to sweet. Aroma — Distinct, complex and highly aromatic. Quality — Best.

*Core.*—Median. Bundle area — Medium small, symmetrical. Halves of area — Equal. Bundles — Inconspicuous. Core lines — Meeting, heart-shaped. Calyx tube — Funnel-form, Pubescence, none. Stem or funnel — Medium long. Depth of tube to shoulder — About 5 mm. Entire depth — About 12 mm. Styles — Some present, united at base. Stamens — Median, in one whorl. Carpels — Closed, axile, symmetrical, smooth, cordate form, emarginate at outer edge near tip. Browning of the flesh (one hour after being cut, with stainless steel knife) — Weak. Firmness of the flesh (measurement with penetrometer) — Firm. Pressure and percent sugar (average of 10 fruit) — Pressure at harvest, 8.1 kg/cm$_3$. % sugar at harvest, 13.6%. Pressure 3-mo cool store, 6.8 kg/cm$_3$. % sugar 3-mo cool store, 13.4%.

Other Characteristics:

*Seeds.*—One or two per cell, not tufted, acute at point, 8-9 mm long, 5 mm wide, obtuse, dark brown (31-15). Winter chill requirements — Estimated winter chilling requirements are less than 400 hours below 7° C. Potentially adaptable to temperature, mediterranean and partially subtropical climate zones. Soluble sugars mg/g dry wt — 698 (29). Soluble sugars mg/g fresh wt — 111 (7). Soluable solids g/100 ml — 13.9 (0.9). Drymatter % — 15.9 (0.8).

| Pollination: | |
|---|---|
| Pollinator | Lady William |
| % Set | 1988 ≈ 55% |
| | 1989 ≈ 0% |
| | 1990 ≈ 50% |
| Pollinator | Hi Early |
| % Set | 1988 ≈ 70% |
| | 1989 ≈ 50% |
| | 1990 ≈ 55% |
| Pollinator | Granny Smith |
| % Set | 1988 ≈ 55% |
| | 1989 ≈ 10% |
| | 1990 ≈ N/A |
| Pollinator | Golden Delicious |

-continued

| Pollination: | |
|---|---|
| % Set | 1988 ≈ 50% |
| | 1989 ≈ 0% |
| | 1990 ≈ 30% |
| Pollinator | Gala |
| % Set | 1988 ≈ 55% |
| | 1989 ≈ 35% |
| | 1990 ≈ 60% |
| Pollinator | Sundowner |
| % Set | 1988 ≈ 25% |
| | 1989 ≈ 10% |

-continued

| Pollination: | |
|---|---|
| | 1990 ≈ 70% |

Use: Dessert, market.

Keeping quality: Good (up to six months in coldroom storage and 10–12 months in C.A. storage) Retail shelf life of approximately four weeks at temperatures of 15–18 degrees C.

What is claimed is:

1. A new variety of apple tree substantially as herein shown and described characterized by its ability to produce high quality dessert type fruits on spurs growing on upright limbs, firm, juicy, creamy-white flesh and excellent storage characteristics.

* * * * *